US010086157B2

(12) United States Patent
Kirby et al.

(10) Patent No.: US 10,086,157 B2
(45) Date of Patent: Oct. 2, 2018

(54) SYSTEM AND METHOD FOR IMPROVED COMPLIANCE IN RESPIRATORY THERAPY

(71) Applicant: KONINKLIJKE PHILIPS N.V., Eindhoven (NL)

(72) Inventors: Mark Todd Kirby, Pottstown, PA (US); Erik Witt, Wychoff, NJ (US)

(73) Assignee: Koninklijke Philips N.V., Eindhoven (NL)

( * ) Notice: Subject to any disclaimer, the term of this patent is extended or adjusted under 35 U.S.C. 154(b) by 883 days.

(21) Appl. No.: 14/414,780

(22) PCT Filed: Jul. 12, 2013

(86) PCT No.: PCT/IB2013/055767
§ 371 (c)(1),
(2) Date: Jan. 14, 2015

(87) PCT Pub. No.: WO2014/013411
PCT Pub. Date: Jan. 23, 2014

(65) Prior Publication Data
US 2015/0174347 A1 Jun. 25, 2015

Related U.S. Application Data

(60) Provisional application No. 61/672,951, filed on Jul. 18, 2012.

(51) Int. Cl.
*A61M 16/00* (2006.01)
*A61M 16/16* (2006.01)
*A61M 16/10* (2006.01)

(52) U.S. Cl.
CPC .... *A61M 16/0003* (2014.02); *A61M 16/0069* (2014.02); *A61M 16/024* (2017.08);
(Continued)

(58) Field of Classification Search
None
See application file for complete search history.

(56) References Cited

U.S. PATENT DOCUMENTS

| 6,988,994 B2 | 1/2006 | Rapoport et al. |
| 7,186,221 B2 | 3/2007 | Rapoport et al. |

(Continued)

FOREIGN PATENT DOCUMENTS

| FR | 2889071 A1 | 2/2007 |
| WO | 2005077447 A1 | 8/2005 |

(Continued)

OTHER PUBLICATIONS

Mitrouska et al, "Effects of Theophylline on Ventilatory Poststimulus Potentiation in Patients With Brain Damage", American Journal of Respiratory Critical Care Medicine, vol. 167, No. 8, 2003, pp. 1124-1130.

(Continued)

Primary Examiner — Rachel T Sippel (57) ABSTRACT

Systems and methods to provide respiratory therapy may determine a target pressure level in a current therapy session on the successful completion and/or compliance of a patient (for example for at least a threshold amount of respiratory therapy) during one or more prior therapy sessions. By gradually increasing the provided pressure level, patients may improve compliance, comfort, and/or other indicators of how well-tolerated the respiratory therapy is for a patient.

12 Claims, 3 Drawing Sheets

(52) U.S. Cl.
CPC ....... *A61M 16/161* (2014.02); *A61M 16/0009* (2014.02); *A61M 2016/0021* (2013.01); *A61M 2016/0027* (2013.01); *A61M 2016/0036* (2013.01); *A61M 2016/102* (2013.01); *A61M 2205/3327* (2013.01); *A61M 2205/3331* (2013.01); *A61M 2205/3365* (2013.01); *A61M 2205/3368* (2013.01); *A61M 2205/502* (2013.01); *A61M 2205/52* (2013.01)

(56) References Cited

U.S. PATENT DOCUMENTS

| | | |
|---|---|---|
| 2005/0038353 A1 | 2/2005 | Rapoport et al. |
| 2006/0009708 A1 | 1/2006 | Rapoport et al. |
| 2006/0102179 A1 | 5/2006 | Rapoport et al. |
| 2007/0017518 A1 | 1/2007 | Farrugia et al. |
| 2007/0055168 A1 | 3/2007 | Rapoport et al. |
| 2007/0227538 A1* | 10/2007 | Scholler .............. A61M 16/024 128/204.18 |
| 2008/0060647 A1* | 3/2008 | Messenger .......... A61M 16/024 128/204.23 |
| 2008/0202528 A1* | 8/2008 | Carter ............... A61M 16/0051 128/204.23 |
| 2008/0245368 A1 | 10/2008 | Dunsmore et al. |
| 2009/0038616 A1 | 2/2009 | Mulcahy et al. |
| 2009/0050154 A1* | 2/2009 | Strothmann ...... A61M 16/0051 128/204.23 |
| 2009/0205662 A1 | 8/2009 | Kwok et al. |
| 2010/0242967 A1* | 9/2010 | Burbank ................... A61F 5/08 128/207.18 |
| 2012/0003620 A1 | 1/2012 | Pittman et al. |
| 2012/0232420 A1* | 9/2012 | Salamitou .............. A61B 5/087 600/538 |
| 2013/0133656 A1* | 5/2013 | Nightingale ...... A61M 16/0066 128/204.23 |

FOREIGN PATENT DOCUMENTS

| | | |
|---|---|---|
| WO | 2006133493 A1 | 12/2006 |
| WO | 2006133495 A1 | 12/2006 |
| WO | 2011048524 A1 | 4/2011 |

OTHER PUBLICATIONS

Lin et al, "Treatment Compliance in Patients Lost to Follow-Up After Polysomnography", Otolaryngology Head and Neck Surgery, vol. 136, 277, pp. 236-240, 2007.

* cited by examiner

SYSTEM AND METHOD FOR IMPROVED COMPLIANCE IN RESPIRATORY THERAPY

CROSS-REFERENCE TO PRIOR APPLICATIONS

This application is the U.S. National Phase application under 35 U.S.C. § 371 of International Application No. PCT/IB2013/055767, filed on Jul. 12, 2013, which claims the benefit of U.S. Provisional Patent Application No. 61/672,951, filed on Jul. 18, 2012. These applications are hereby incorporated by reference herein.

The present disclosure pertains to a system and method for providing respiratory therapy through a pressure support device, and, in particular, to improving compliance by gradually increasing one or more pressure levels used during respiratory therapy.

It is well known that some types of respiratory therapy involve the delivery of a flow of breathable gas to the airway of a subject, for example through a positive airway pressure device. It is known that a flow of breathable gas may be pressurized at varying levels of pressure, even during a single therapy session. It is known that one or more algorithms may operate to control and/or adjust the pressure level used in respiratory therapy. It is known that measurements or estimations of various gas parameters can be used in a feedback manner to control and/or adjust the pressure level used in respiratory therapy. It is known that increased pressure levels may not be very comfortable for subjects, in particular subjects that are relatively new to using a positive airway pressure device. It is known that compliance to a respiratory therapy regimen is related to comfort and ease-of-use.

Accordingly, it is an object of one or more embodiments of the present invention to provide a system for providing respiratory therapy to a subject having an airway. The system comprises a pressure generator, one or more sensors, one or more processors, a compliance module, a target module, and a control module. The pressure generator is configured to generate a pressurized flow of breathable gas for delivery to the airway of the subject. The one or more sensors are configured to generated output signals conveying information related to one or more gas parameters of the pressurized flow of breathable gas. The one or more processors are configured to execute processing modules. The compliance module is configured to determine whether the subject successfully completes a threshold amount of respiratory therapy during therapy sessions. The target module is configured to determine a target pressure for the pressurized flow of breathable gas during a current therapy session. The target pressure is based on a prescribed therapy regimen and determinations by the compliance module pertaining to prior therapy sessions. The control module is configured to adjust levels of one or more gas parameters of the pressurized flow of breathable gas based on the determined target pressure.

It is yet another aspect of one or more embodiments of the present invention to provide method for providing respiratory therapy to a subject having an airway. The method comprises generating a pressurized flow of breathable gas for delivery to the airway of the subject; generating output signals conveying information related to one or more gas parameters of the pressurized flow of breathable gas; determining a compliance determination, wherein the compliance determination is based on whether the subject successfully completes a threshold amount of respiratory therapy during a first therapy session; determining a target pressure for the pressurized flow of breathable gas during a second therapy session subsequent to the first therapy session, wherein the target pressure is based on a prescribed therapy regimen and the compliance determination pertaining to the first therapy session; and adjusting levels of one or more gas parameters of the pressurized flow of breathable gas based on the determined target pressure.

It is yet another aspect of one or more embodiments to provide a system configured for providing respiratory therapy to a subject having an airway. The system comprises means for generating a pressurized flow of breathable gas for delivery to the airway of the subject; means for generating output signals conveying information related to one or more gas parameters of the pressurized flow of breathable gas; means for determining a compliance determination, wherein the compliance determination is based on whether the subject successfully completes a threshold amount of respiratory therapy during a first therapy session; means for determining a target pressure for the pressurized flow of breathable gas during a second therapy session subsequent to the first therapy session, wherein the target pressure is based on a prescribed therapy regimen and the compliance determination pertaining to the first therapy session; and means for adjusting levels of one or more gas parameters of the pressurized flow of breathable gas based on the determined target pressure.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
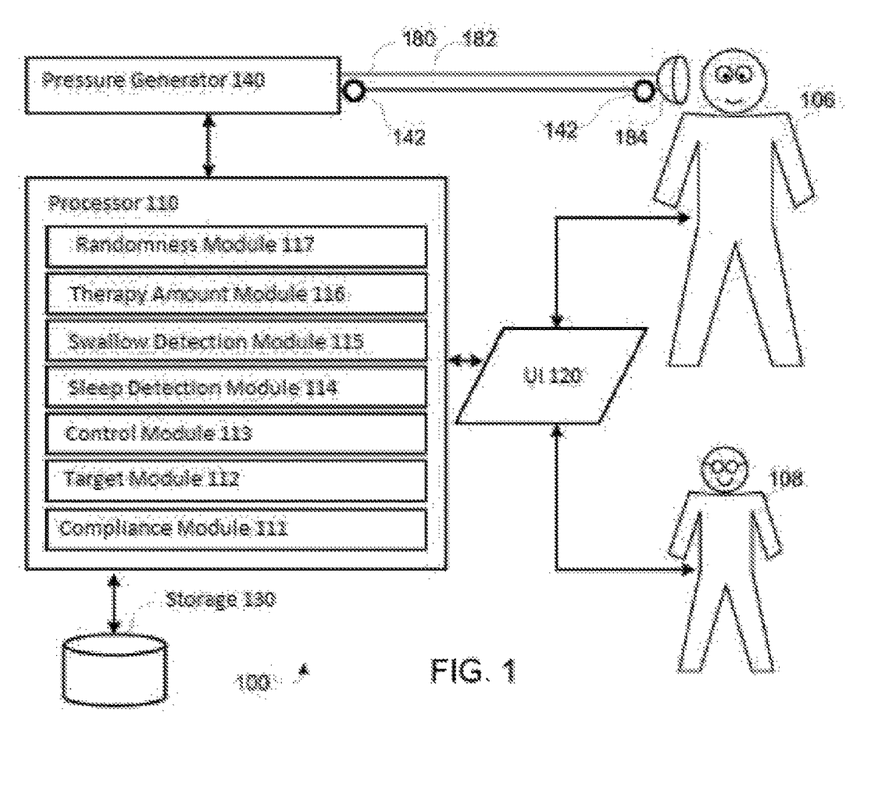
FIG. 1 schematically illustrates a system for providing respiratory therapy to a subject in accordance with one or more embodiments.

FIG. 1 schematically illustrates a system 100 for providing respiratory therapy to a subject 106. System 100 may be implemented as, integrated with, and/or operating in conjunction with a respiratory therapy device. System 100 measures, determines, and/or estimates whether a subject successfully completed at least a threshold amount of respiratory therapy during a therapy session, and bases the pressure level of a pressure flow of breathable gas thereon. System 100 gradually increases the provided pressure level in order to improve the quality, comfort, effectiveness, and/or long-term results of the respiratory therapy.

A therapy "session" of using system 100 may be defined as a period of substantially uninterrupted therapeutic usage of system 100, not to exceed some upper threshold of (consecutive) hours. The upper threshold may be, for example, about 10 hours, about 12 hours, about 16 hours, about 24 hours and/or other time periods. If the respiratory therapy is used to treat sleeping disorders, the related session length may correspond to the sleeping pattern of a subject. A typical session length may thus be about eight hours. Alternatively, and/or simultaneously, a therapy session may be defined as a period of substantially uninterrupted therapeutic usage of system 100, not to span less than some lower threshold of (consecutive) units of time, and/or at least a minimum period of time apart from a previous session. The lower threshold may be, for example, about 15 minutes, about 30 minutes, about 1 hour, about 2 hours, about 3 hours, about 4 hours, about 5 hours and/or other time periods. For example, a minute of usage may be too short to be regarded as a session. For example, two 3-hour periods of usage separated by a 10-minute gap may be regarded as one session rather than two sessions. Individual therapy sessions may have a beginning and an end. Individual therapy sessions may form a sequence of therapy sessions, such that the current therapy sessions may be distinguished from one or more prior therapy sessions. Prior therapy sessions may also be referred to as previous therapy sessions.

In some embodiments, one or more operative levels (e.g. pressure, volume, etc.) are adjusted on a relatively ongoing manner (e.g., between individual breaths, every few breaths, every few seconds, every minute, etc.) during an individual therapy session to titrate the therapy.

System 100 includes one or more of a pressure generator 140, a delivery circuit 180, one or more sensors 142, an electronic storage 130, a user interface 120, a processor 110, a compliance module 111, a target module 112, a control module 113, a sleep detection module 114, a swallow detection module 115, and/or other components.

Pressure generator 140 of system 100 in FIG. 1 may be integrated, combined, coupled, and/or connected with a (positive) airway pressure device (PAP/CPAP/BiPAP®/etc.). Pressure generator 140 may be configured to provide a pressurized flow of breathable gas for delivery to the airway of subject 106, e.g. via an output or outlet of pressure generator 140, and/or via a delivery circuit 180. Delivery circuit 180 may sometimes be referred to as subject interface 180. Subject 106 may initiate one or more phases of respiration. Respiratory therapy may be implemented as pressure control, pressure support, volume control, and/or other types of support and/or control. For example, to support inspiration, the pressure of the pressurized flow of breathable gas may be adjusted to an inspiratory pressure. Alternatively, and/or simultaneously, to support expiration, the pressure and/or flow of the pressurized flow of breathable gas may be adjusted to an expiratory pressure. Adjustments may be made numerous times in implementations using auto-titrating for providing respiratory support through the delivery of the pressurized flow of breathable gas. In addition to alternating between multiple levels, the inhalation pressure level may ramp up or down according to a predetermined slope (absolute and/or relative, e.g. dependent on breathing rate) for any specified section of a phase. Similar features may be available for exhalation phases. The pressure levels may be either predetermined and fixed, follow a predetermined dynamic characteristic, or they may dynamically change from breath-to-breath or night-to-night depending on sensed breathing, breathing disorder, or other physiological characteristics. Pressure generator 140 is configured to adjust one or more of pressure levels, flow, humidity, velocity, acceleration, and/or other parameters of the pressurized flow of breathable gas, e.g. in substantial synchronization with the breathing cycle of subject 106.

A positive airway pressure device may be configured such that one or more gas parameters of the pressurized flow of breathable gas are controlled in accordance with a therapeutic respiratory regimen for subject 106. The one or more gas parameters include one or more of flow, volume, retrograde volume, pressure, humidity, velocity, acceleration, (intentional) gas leak, and/or other parameters. System 100 may be configured to provide types of therapy including therapy where a subject performs inspiration and/or expiration of his own accord and/or where the device provides negative airway pressure.

A pressurized flow of breathable gas is delivered from pressure generator 140 to the airway of subject 106 via a delivery circuit 180. Delivery circuit 180 may include a conduit 182 and/or a subject interface appliance 184. Conduit 182 may include a flexible length of hose, or other conduit, either in single-limb or dual-limb configuration that places subject interface appliance 184 in fluid communication with pressure generator 140. Conduit 182 forms a flow path through which the pressurized flow of breathable gas is communicated between subject interface appliance 184 and pressure generator 140. Conduit 182 may comprise a standard 22 mm diameter hose (other common diameters range between ¾" and 1") or, in certain embodiments, a much smaller diameter hose that is in the range of • of a standard size hose. Such a hose, which may be referred to as a restricted flow hose or limited flow hose, (for example, having a diameter ranging between ¼" and •", or alternatively between 6 mm and 9 mm) has a greater resistance to gas flow and allows/requires a lower peak flow, typically of less than 50% compared to a standard size hose (in some embodiments between 20%-30% of the peak flow through a standard size hose). Less flow and less energy are required when using a smaller hose to operate the system, in a manner described herein, to provide respiratory therapy. Additionally, such a system may be smaller and/or less obtrusive.

Subject interface appliance 184 of system 100 in FIG. 1 is configured to deliver the pressurized flow of breathable gas to the airway of subject 106. As such, subject interface appliance 184 may include any appliance suitable for this function. In some embodiments, subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full-face mask, a total facemask, and/or other interface appliances that communicate a flow of gas with an airway of a subject. The present disclosure is not limited to these examples, and contemplates delivery of the pressurized flow of breathable gas to subject 106 using any subject interface.

Electronic storage 130 of system 100 in FIG. 1 comprises electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. For example, electronic storage 130 may record or store timing information (including duration of inhalation phases and exhalation phases as well as transitional moments), one or more (breathing) parameters and/or other parameters (as discussed elsewhere herein), pressure levels, information indicating whether the subject successfully completed at least a threshold amount of prescribed respiratory therapy, information indicating whether a respiratory event (including Cheyne-Stokes respiration, central sleep apnea, obstructive sleep apnea, hypopnea, snoring, hyperventilation, and/or other respiratory events) occurred, information indicating adequacy of treatment, and/or other information. For example, stored information may be organized per day, per week, per therapy session, and/or in other ways. Electronic storage 130 may be a separate component within system 100, or electronic storage 130 may be provided integrally with one or more other components of system 100 (e.g., processor 110).

User interface 120 of system 100 in FIG. 1 is configured to provide an interface between system 100 and a user (e.g., user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. An example of information that may be conveyed to user 108 is a report detailing compliance information and/or occurrences of respiratory events throughout a period during which the subject is receiving therapy. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

One or more sensors 142 of system 100 in FIG. 1 are configured to generate output signals conveying measurements related to gas parameters of respiratory airflow, parameters related to airway mechanics, and/or other parameters. Gas parameters may include flow, (airway) pressure, humidity, velocity, acceleration, and/or other gas parameters. Output signals may convey measurements related to respiratory parameters. Sensor 142 may be in fluid communication with conduit 182 and/or subject interface appliance 184. Sensor 142 may generate output signals related to physiological parameters pertaining to subject 106. Parameters may be associated with the state and/or condition of an airway of subject 106, the breathing of subject 106, the gas breathed by subject 106, the composition of the gas breathed by subject 106, the delivery of the gas to the airway of subject 106, and/or a respiratory effort by the subject. For example, a parameter may be related to a mechanical unit of measurement of a component of pressure generator 140 (or of a device that pressure generator 140 is integrated, combined, or connected with) such as valve drive current, rotor speed, motor speed, blower speed, fan speed, or a related measurement that may serve as a proxy for any of the parameters listed herein through a previously known and/or calibrated mathematical relationship.

The illustration of sensor 142 including two members in FIG. 1 is not intended to be limiting. In some hardware configurations, system 100 may use only one sensor 142. The individual sensor 142 may be located at or near subject interface appliance 184, or at other locations. In some hardware configurations, system may include a sensor 142 at or near an output of pressure generator 140. The illustration of a sensor 142 at or near subject interface appliance 184 and a sensor 142 at or near an output of pressure generator 140 is not intended to be limiting. Resulting signals or information from one or more sensors 142 may be transmitted to processor 110, user interface 120, electronic storage 130, and/or other components of system 100. This transmission may be wired and/or wireless.

The one or more sensors 142 may be configured to generate output signals in an ongoing manner during a therapy session. This may include generating signals intermittently, periodically (e.g. at a sampling rate), continuously, continually, at varying intervals, and/or in other ways that are ongoing during at least a portion of a therapy session. For example, in some embodiments, the generated output signals may be considered as a vector of output signals, such that a vector includes multiple samples of information conveyed related to one or more gas parameters and/or other parameters. Different parameters may be related to different vectors. A particular parameter determined in an ongoing manner from a vector of output signals may be considered as a vector of that particular parameter.

Processor 110 of system 100 in FIG. 1 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some embodiments, processor 110 includes a plurality of processing units.

As is shown in FIG. 1, processor 110 is configured to execute one or more computer program modules. The one or more computer program modules include one or more of compliance module 111, target module 112, control module 113, sleep detection module 114, swallow detection module 115, therapy amount module 116, randomness module 117, and/or other modules. Processor 110 may be configured to execute modules 111-117 by software; hardware; firmware; some combination of software, hardware, and/or firmware; and/or other mechanisms for configuring processing capabilities on processor 110.

It should be appreciated that although modules 111-117 are illustrated in FIG. 1 as being co-located within a single processing unit, in embodiments in which processor 110 includes multiple processing units, one or more of modules 111-117 may be located remotely from the other modules. The description of the functionality provided by the different modules 111-117 described herein is for illustrative purposes, and is not intended to be limiting, as any of modules 111-117 may provide more or less functionality than is described. For example, one or more of modules 111-117 may be eliminated, and some or all of its functionality may be incorporated, shared, integrated into, and/or otherwise provided by other ones of modules 111-117. Note that processor 110 may be configured to execute one or more additional modules that may perform some or all of the functionality attributed below to one of modules 111-117.

One or more modules of system 100 in FIG. 1 may be configured to determine one or more gas parameters, breathing parameters, and/or other parameters from output signals generated by sensor(s) 142, for example in an ongoing manner. The one or more gas parameters may include and/or be related to one or more of (peak) flow rate, flow rate, (tidal) volume, pressure, temperature, humidity, velocity, acceleration, gas composition (e.g. concentration(s) of one or more constituents such as, e.g., $CO_2$), thermal energy dissipated, (intentional) gas leak, and/or other measurements related to the (pressurized) flow of breathable gas. One or more gas parameters may be determined at different locations and/or positions within system 100, including within pressure generator 140, at or near an output of pressure generator 140, within subject interface 180, at or near the point of engagement between pressure generator 140 and subject interface 180, within conduit 182, at or near an input of conduit 182, at or near an output of conduit 182, within subject interface appliance 184, at or near an input of subject interface appliance 184, at or near an output of subject interface appliance 184, and/or at other locations and/or positions within system 100.

One or more modules of system 100 may derive one or more breathing parameters from one or more determined gas parameters and/or generated output signals. The one or more breathing parameters may include one or more of respiratory rate, breathing period, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), and/or other breathing parameters. Alternatively, and/or simultaneously, vectors of parameters may be derived in an ongoing manner during a therapy session from vectors of generated output signals and/or other (vectors of) determined parameters.

Therapy amount module 116 is configured to determine the amount of provided respiratory therapy subject 106 completed successfully during therapy sessions. The amount may be determined on a per-session basis. In some embodiments, the amount of respiratory therapy may be cumulative, such that multiple shorter periods of successful completion with the provided respiratory therapy may be added together to reach a total amount for a particular therapy session, so long as the shorter periods are part of the same therapy session. Alternatively, and/or simultaneously, in some embodiments, the amount of respiratory therapy may need to be reached in a consecutive, continuous, and/or substantially uninterrupted manner within one therapy session. Combinations and/or variations of both approaches to determine the total amount per therapy session are considered within the scope of this disclosure. Various and varying standards to determine whether respiratory therapy is considered "completed successfully" may be implemented. Successful completion may for example be based on detecting whether subject 106 removed subject appliance interface 184 during respiratory therapy. Successful completion may for example be based on one or more of detections of occurrences of respiratory events, determinations of randomness and/or variability in breathing patterns (e.g. by randomness module 117), detections of occurrences of temporary flow limitations, and/or other factors. Determinations by therapy amount module 116 may be performed and/or updated in an ongoing manner during a therapy session.

Compliance module 111 is configured to obtain a threshold amount of respiratory therapy, e.g. through user interface 120. Compliance module 111 is further configured to determine whether subject 106 successfully completed at least a threshold amount of respiratory therapy during a therapy session by comparing the obtained threshold amount to an amount as determined by therapy amount module 116.

Determinations by compliance module 111 may be referred to as compliance determinations. The threshold amount may be 1 hour, 2 hours, 3 hours, 4 hours, 5 hours, 6 hours, and/or another amount of respiratory therapy.

Randomness module 117 may be configured to determine a measure of randomness in the breathing pattern of subject 106 during at least part of a therapy session. Randomness may be determined through statistical analysis of a variability (and/or other statistical operation) of the duration of inhalations, the duration of exhalations, any other breathing parameter, and/or combinations thereof. If respiratory therapy is well-tolerated, the randomness may be lower than moments or periods during which the respiratory therapy is not well-tolerated. If subject 106 is struggling to endure and/or undergo a particular type or setting of provided respiratory therapy, the determined randomness in the breathing pattern may indicate this in a quantitative manner.

In some embodiments, a patient-specific baseline for a measure of randomness may be determined during a low level of pressure or even no pressure. Such a baseline of randomness may subsequently be compared, during a subsequent therapy session, with a randomness in the breathing pattern during at least part of the subsequent therapy session. A particular increase in randomness may indicate that the current respiratory therapy (e.g. at the current pressure level)

is not well-tolerated, not comfortable, not completed successfully, and/or not compliant for the purpose of a determination by compliance module 111. In some implementations, compliance determinations by compliance module 111 may be based on one or more determinations by randomness module 117. Determinations by randomness module 117 may be performed and/or updated in an ongoing manner during a therapy session.

Figure 2A:
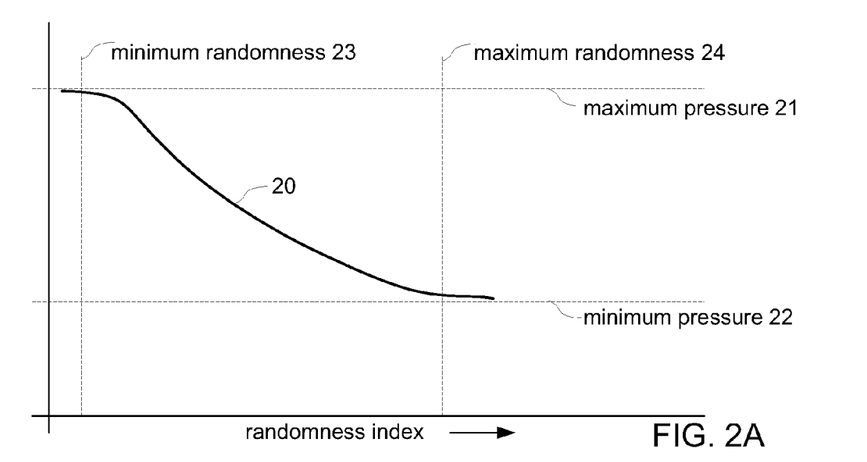
FIG. 2A illustrates a graph of randomness versus pressure level in accordance with one or more embodiments.

By way of illustration, FIG. 2A illustrates a graph 20 of a randomness index (along the X-axis) in a breathing pattern of a particular subject versus pressure level (along the Y-axis) of, e.g., a pressurized flow of breathable gas being provided during respiratory therapy. Minimum pressure 22 may indicate a lower threshold for a target pressure level for respiratory therapy, or a pressure offset to be applied to a target pressure level being provided during a therapy session. Maximum pressure 21 may indicate an upper threshold for a target pressure level for respiratory therapy, or a pressure offset to be applied to a target pressure level being provided during a therapy session. As indicated in FIG. 2A, responsive to a measured, determined, and/or estimated randomness in the breathing pattern of a particular subject during a given therapy session at or near the value of a minimum randomness 23, e.g. a baseline randomness as established using the provision of no or low pressure, (and possibly in conjunction with one or more other factors and/or considerations) the system and/or an algorithm described herein (see FIG. 2B) may be configured to determine that the particular subject successfully completed respiratory therapy at the target pressure level and may further be configured to adjust the target pressure for one or more subsequent therapy sessions. For example, the current target pressure level may be increased and/or offset by a value similar to and/or the same as maximum pressure 21 for the subsequent therapy session. Alternatively, and/or simultaneously, a compliance determination may be favorably affected by a low index of randomness, for example such that a smaller amount of respiratory therapy qualifies as being compliant in conjunction with a low index of measured, determined, and/or estimated randomness.

As further indicated in FIG. 2A, responsive to a measured, determined, and/or estimated randomness in the breathing pattern of a particular subject during a given therapy session at or near the value of a maximum randomness 24, (and possibly in conjunction with one or more other factors and/or considerations) the system and/or an algorithm described herein (see FIG. 2B) may be configured to determine that the particular subject successfully completed respiratory therapy at the target pressure level and may further be configured to adjust the target pressure for one or more subsequent therapy sessions. For example, the current target pressure level may be decreased and/or offset by a value similar to and/or the same as minimum pressure 22 for the subsequent therapy session. Alternatively, and/or simultaneously, a compliance determination may be negatively affected by a high index of randomness, for example such that a threshold amount of respiratory therapy fails to qualify as being compliant in conjunction with a high index of measured, determined, and/or estimated randomness.

Target module 112 is configured to determine a target pressure for the pressurized flow of breathable gas during a current therapy session. The target pressure may be in accordance with a therapy regimen, and may dynamically change and/or titrate during one or more therapy sessions. For example, the therapy regimen may prescribe a particular pressure level. The target pressure may further be based on one or more determinations by compliance module 111 pertaining to one or more prior therapy sessions. For example, target module 112 may start therapy using a below-prescription pressure level (such as e.g. a minimum pressure level) as the target pressure that is below the prescribed pressure level. Responsive to subject 106 successfully completing a threshold amount of respiratory therapy during one or more therapy sessions using the below-prescription pressure level, target module 112 may gradually increase the target pressure level for subsequent therapy sessions, e.g. using small increments such as 1 cm-H$_2$O. Through repeated and gradual increments of the target pressure level over the course of multiple therapy sessions, and assuming continued successful completion by subject 106 as described previously, the target pressure determined by target module 112 will eventually reach the prescribed pressure level of the therapy regimen. In some embodiments, responsive to subject 106 failing to successfully complete at least a threshold amount of respiratory therapy during a particular therapy session at a particular target pressure level, target module 112 may be configured to maintain and/or reduce the target pressure level for a subsequent therapy session, which may depend on the value of the current target pressure level in relation to the prescribed pressure level. Target module 112 may be configured to implement an algorithm to determine the target pressure, as well as increasing and/or reducing the target pressure, as described herein. The target pressure may be adjusted as the prescribed pressure level changes.

Figure 2B:
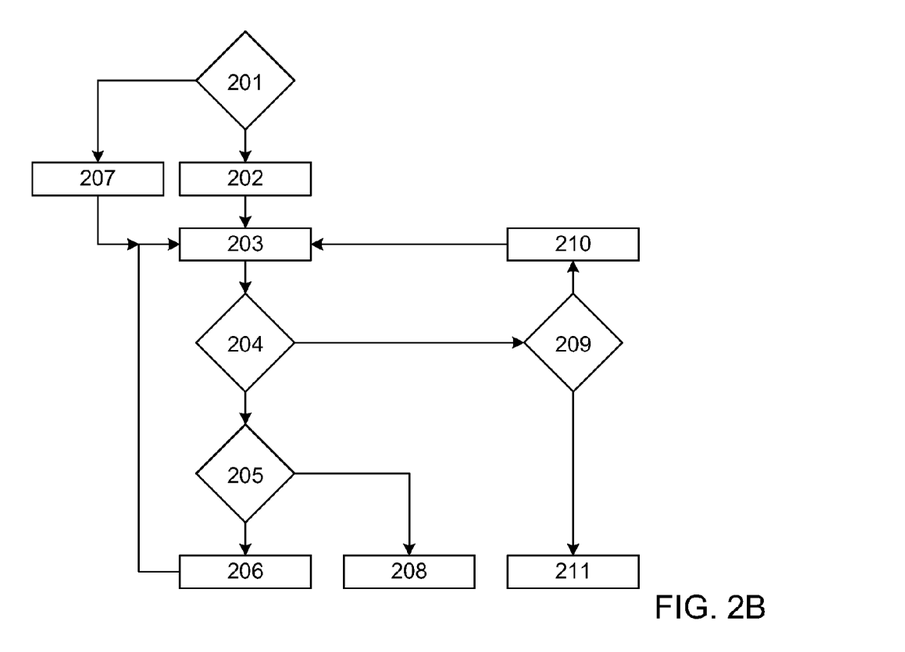
FIG. 2B illustrates an algorithm used to provide respiratory therapy in accordance with one or more embodiments.

By way of illustration, FIG. 2B illustrates an exemplary algorithm used to provide respiratory therapy to a particular subject, and, in particular, to determine a target pressure level for a current therapy session. Note that similar algorithms using more or fewer steps may be envisioned within the scope of this disclosure. Note that the examples provided in relation to FIG. 2B are not intended to be limiting in any way. At a step 201, the prescribed pressure level is checked against a threshold level of, for example, 11 cm-H2O. Other threshold levels are contemplated. If the prescribed pressure level is higher than the threshold level, the algorithm may continue at a step 202, otherwise at a step 207. At step 207, the target pressure level is set to the prescribed pressure level. At step 202, the target pressure level is set to a predetermined fraction of the prescribed pressure level, such as 50%. Other fractions or functions of the prescribed pressure level are contemplated. After step 207 and/or step 202, the algorithm may continue at a step 203. At step 203, the target pressure level is used to provide a pressurized flow of breathable gas during the current therapy session. In some embodiments, a therapy session may coincide with provided respiratory therapy during an entire night, e.g. covering all or most of the period the particular subject is sleeping. After step 203, the algorithm may continue at a step 204. At step 204, compliance by the particular subject is checked to verify whether the particular subject successfully completed at least a threshold amount of respiratory therapy during the therapy session provided and/or administered during step 203. If the particular subject was successful, as determined at step 204, the algorithm may continue at a step 205, otherwise at a step 209. At step 209, the current target pressure level is checked against a lower threshold level of, for example, 5 cm-H2O. Other lower threshold levels are contemplated. If the current target pressure level is below the lower threshold level, the algorithm may continue at a step 211, otherwise at a step 210. At step 211, a healthcare provider and/or other qualified medical personnel may be notified. At step 210, the target pressure level may be reduced, e.g. by an amount of 1 cm-H2O. Other fixed and/or variable amounts for reducing the target pressure level are contemplated. Responsive to this reduction, the algorithm may continue at step 203 for a subsequent therapy session. At step 205, responsive to the particular subject successfully completing at least a threshold amount of respiratory therapy as determined at step 204, the current target pressure may be compared to the prescribed pressure level. If these pressure levels are equal and/or similar, the algorithm may continue at a step 208, indicating standard respiratory therapy. Otherwise, the algorithm may continue at a step 206. Step 206 the target pressure level may be increased, e.g. by an amount of 1 cm-H2O. Other fixed and/or variable amounts for increasing the target pressure level are contemplated. Responsive to this increase, the algorithm may continue at step 203 for a subsequent therapy session.

Control module 113 is configured to control operation of system 100 during therapy sessions. Control module 113 may be configured to control the pressure generator to adjust one or more levels of gas parameters of the pressurized flow of breathable gas in accordance with one or more of a (respiratory) therapy regimen, based on one or more target pressures determined by target module 112, based on one or more algorithms that control adjustments and/or changes in the pressurized flow of breathable gas (including, e.g., the algorithm described in relation to FIG. 2B), and/or based on other factors. Referring to FIG. 1, control module 113 may be configured to control pressure generator 140 to provide the pressurized flow of breathable gas. Control module 113 may be configured to control pressure generator 140 such that one or more gas parameters of the pressurized flow of breathable gas are varied over time in accordance with a respiratory therapy regimen.

One or more parameters based on output signals generated by sensors 142 may be used by control module 113, e.g. in a feedback manner, to adjust one or more therapy modes/settings/operations of system 100. Alternatively, and/or simultaneously, signals and/or information received through user interface 120 may be used by control module 113, e.g. in a feedback manner, to adjust one or more therapy modes/settings/operations of system 100. Control module 113 may be configured to time its operations relative to transitional moments in the breathing cycle of a subject, over multiple breath cycles, and/or in any other timing relation.

Sleep detection module 114 is configured to detect sleep onset of subject 106. Determinations of the target pressure by target module 112 may further be based on whether sleep onset has been detected. For example, once sleep onset has been detected, the target pressure may be gradually increased in order to build up tolerance to increased pressure levels for respiratory therapy. Increased and/or improved tolerance may improve compliance. The target pressure may be decreased to the pre-sleep level once subject 106 is detected to be awake.

Swallow detection module 115 is configured to detect swallowing by subject 106. Since swallowing air, or aerophagia, may contribute to a reduced level of comfort and/or compliance, the target pressure may be temporarily reduced by target module 112 during the process of swallowing by subject 106 in order to reduce aerophagia, and thus improve compliance.

Figure 3:
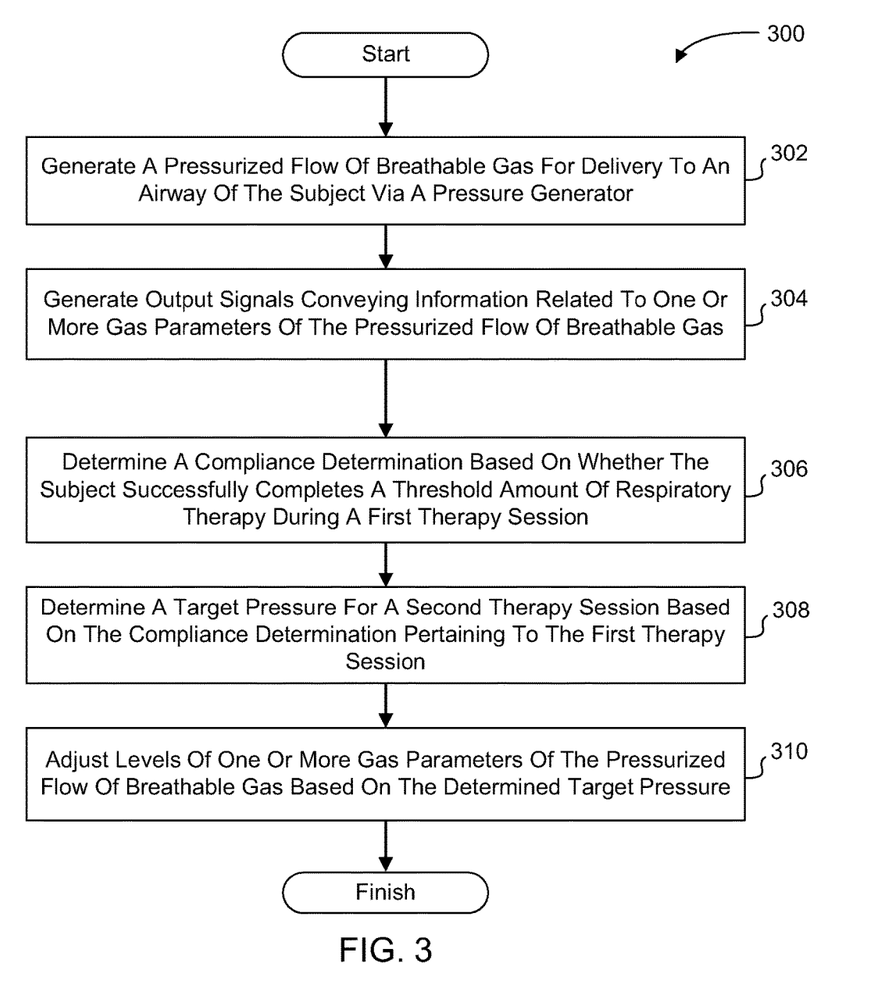
FIG. 3 illustrates a method for providing respiratory therapy to a subject.

FIG. 3 illustrates a method 300 for providing respiratory therapy to a subject. The operations of method 300 presented below are intended to be illustrative. In certain embodiments, method 300 may be accomplished with one or more additional operations not described, and/or without one or more of the operations discussed. Additionally, the order in which the operations of method 300 are illustrated in FIG. 3 and described below is not intended to be limiting.

In certain embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, a pressurized flow of breathable gas is generated for delivery to the airway of the subject via an output of the pressure generator. In some embodiments, operation 302 is performed by a pressure generator similar to or substantially the same as pressure generator 140 (shown in FIG. 1 and described herein).

At an operation 304, output signals conveying information related to one or more gas parameters of the pressurized flow of breathable gas are generated. In some embodiments, operation 304 is performed by one or more sensors similar to or substantially the same as one or more sensors 142 (shown in FIG. 1 and described herein).

At an operation 306, a compliance determination is determined. The compliance determination is based on whether the subject successfully completes a threshold amount of respiratory therapy during a first therapy session. In some embodiments, operation 306 is performed by a compliance module similar to or substantially the same as compliance module 111 (shown in FIG. 1 and described herein).

At an operation 308, a target pressure is determined for the pressurized flow of breathable gas during a second therapy session subsequent to the first therapy session. The target pressure is based on a prescribed therapy regimen and the compliance determination pertaining to the first therapy session. In some embodiments, operation 308 is performed by a target module similar to or substantially the same as target module 112 (shown in FIG. 1 and described herein).

At an operation 310, levels of one or more gas parameters of the pressurized flow of breathable gas are adjusted based on the determined target pressure. In some embodiments, operation 310 is performed by a control module similar to or substantially the same as control module 113 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system for providing respiratory therapy to a subject having an airway, the system comprising:
   a pressure generator configured to generate a pressurized flow of breathable gas for delivery to the airway of the subject;
   one or more sensors configured to generated output signals conveying information related to one or more gas parameters of the pressurized flow of breathable gas;
   one or more processors configured to execute processing modules, the processing modules comprising:
   a compliance module configured to determine an amount of respiratory therapy that the subject received during a first therapy session, wherein the compliance module is further configured to determine whether the amount meets and/or passes a threshold amount of respiratory therapy;
   a target module configured to determine a target pressure for the pressurized flow of breathable gas during therapy sessions based on a prescribed therapy regimen and determinations by the compliance module pertaining to prior therapy sessions such that, for a second therapy session subsequent to the first therapy session, the target module determines the target pressure for the pressurized flow of breathable gas based on one or more determinations, by the compliance module pertaining to the first therapy session;
   a control module configured to adjust levels of one or more gas parameters of the pressurized flow of breathable gas based on the determined target pressure; and
   a randomness module configured to determine a measure of randomness in a breathing pattern of the subject during the first therapy session based on analysis of durations of inhalations during the first therapy session,
   wherein determinations by the compliance module are based on the measure of randomness determined by the randomness module, wherein (i) responsive to a first determination that the measure of randomness is below a first threshold of randomness, the target module is configured to increase the target pressure and/or the compliance module is configured to decrease the threshold amount of respiratory therapy and (ii) responsive to a second determination that the measure of randomness is above a second threshold of randomness, the target module is configured to decrease the target pressure and/or the compliance module is configured to increase the threshold amount of respiratory therapy.

2. The system of claim 1, wherein determinations by the compliance module are based on comparisons between measures of randomness determined during multiple therapy sessions.

3. The system of claim 1, further comprising:
   a sleep detection module configured to detect sleep onset, wherein determinations of the target pressure by the target module are further based on whether sleep onset has been detected.

4. The system of claim 1, further comprising:
   a swallow detection module configured to detect swallowing by the subject, wherein the target module is further configured to temporarily reduce the target pressure to reduce aerophagia.

5. A method for compliance determination regarding respiratory therapy of a subject having an airway, the method comprising:
   generating output signals conveying information related to one or more gas parameters of a pressurized flow of breathable gas that is delivered to the airway of the subject;
   determining an amount of respiratory therapy that the subject received during a first therapy session;
   determining a compliance determination, wherein the compliance determination is based on whether the amount meets and/or passes a threshold amount of respiratory therapy;
   determining a target pressure for the pressurized flow of breathable gas during a second therapy session subsequent to the first therapy session, wherein the target pressure is based on a prescribed therapy regimen and the compliance determination pertaining to the first therapy session;
   determining a measure of randomness in a breathing pattern of the subject during the first therapy session based on analysis of durations of inhalations, wherein the compliance determination is based on the measure of randomness,
   increasing the target pressure and/or decreasing the threshold amount of respiratory therapy, responsive to determining that the measure of randomness is below a first threshold of randomness; and
   decreasing the target pressure and/or increasing the threshold amount of respiratory therapy, responsive to determining the measure of randomness is above a second threshold of randomness.

6. The method of claim 5, wherein the compliance determination is further based on a comparison between measures of randomness determined during multiple therapy sessions.

7. The method of claim 5, further comprising:
   detecting sleep onset, wherein determination of the target pressure is further based on whether sleep onset has been detected.

8. The method of claim 5, further comprising:
   detecting swallowing by the subject, wherein the target pressure is temporarily reduced to reduce aerophagia.

9. A system configured for providing respiratory therapy to a subject having an airway, the system comprising:
   means for generating a pressurized flow of breathable gas for delivery to the airway of the subject;
   means for generating output signals conveying information related to one or more gas parameters of the pressurized flow of breathable gas;
   means for determining an amount of respiratory therapy that the subject received during a first therapy session;
   means for determining a compliance determination, wherein the compliance determination is based on whether the amount meets and/or passes a threshold amount of respiratory therapy;
   means for determining a target pressure for the pressurized flow of breathable gas during a second therapy session subsequent to the first therapy session, wherein the target pressure is based on a prescribed therapy regimen and the compliance determination pertaining to the first therapy session;
   means for adjusting levels of one or more gas parameters of the pressurized flow of breathable gas based on the determined target pressure;

means for determining a measure of randomness in a breathing pattern of the subject during the first therapy session based on analysis of durations of inhalations, means for, responsive to determining the measure of randomness is below a first threshold of randomness, increasing the target pressure and/or decreasing the threshold amount of respiratory therapy, and means for, responsive to determining the measure of randomness is above a second threshold of randomness, decreasing the target pressure and/or increasing the threshold amount of respiratory therapy.

10. The system of claim 9, wherein the compliance determination is further based on a comparison between measures of randomness determined during multiple therapy sessions.

11. The system of claim 9, further comprising:

means for detecting sleep onset, wherein determination of the target pressure is further based on whether sleep onset has been detected.

12. The system of claim 9, further comprising:

means for detecting swallowing by the subject, wherein the means for determining a target pressure for the pressurized flow of breathable gas is further configured to temporarily reduce the target pressure to reduce aerophagia.

\* \* \* \* \*